United States Patent [19]

Willman

[11] Patent Number: 5,515,533
[45] Date of Patent: May 7, 1996

[54] PHYSICAL PROPERTY DATABASE RETRIEVAL SYSTEM

[76] Inventor: Todd J. Willman, P.O. Box 270, Woodsfield, Ohio 43793

[21] Appl. No.: 34,303

[22] Filed: Mar. 22, 1993

[51] Int. Cl.$^6$ .................................................. G06F 7/08
[52] U.S. Cl. .............................. 395/600; 395/156
[58] Field of Search .................................. 364/509, 510, 364/420, 413.02, 146, 188; 395/425, 600, 934, 100, 155, 156; 73/155

[56] References Cited

U.S. PATENT DOCUMENTS

| | | | |
|---|---|---|---|
| 4,939,689 | 7/1990 | Davis et al. | 364/600 |
| 4,992,942 | 2/1991 | Bauerle et al. | 364/420 |
| 5,172,332 | 12/1992 | Hungerford et al. | 264/510 |
| 5,247,666 | 9/1993 | Buckwold | 395/600 |
| 5,265,247 | 11/1993 | Wienck et al. | 395/600 |
| 5,329,811 | 7/1994 | Schultz et al. | 73/155 |
| 5,331,548 | 7/1994 | Rollema et al. | 364/413.02 |

*Primary Examiner*—Emanuel T. Voeltz
*Assistant Examiner*—Edward Pipala

*Attorney, Agent, or Firm*—Carothers & Carothers

[57] ABSTRACT

A system to retrieve fluid property data consisting of a single common fluid property database interface and unique files to allow for efficient retrieval of fluid property data from the AIChE DIPPR database or any other fluid properties database from the hard disk storage area of a general data processor. A text file (1) of fluid descriptions for each fluid category is used to define the selections in the fluid description list box (4). A text file (2) of fluid properties for each fluid property category is used to define the selections in the fluid property list box (5). The selections in each list box change according to the category of fluid description and fluid property that is selected. A Get DIPPR Data command (6) then retrieves all fluid property data for the selected fluid description and fluid property in one reading of the AIChE DIPPR database or any other fluid properties database of similar format by utilizing a unique record number reference file (3) so that only the selected fluid's data is read from the database. This provides for quick and easy access to DIPPR fluid property database information that is vital for optimal system design and system operation in the process industries.

1 Claim, 3 Drawing Sheets

Figure 1: Creation of Fluid Description List Files:

[A "Description.Dat" file is created for each category of fluid property desription of format TYPE$ using the following code on the database.]
```
Dim RECORD as String * 80
Open "SOURCE.DAT" for Random as #1 Len=80
Open "Description.Dat" for Output as #2
Loop1: Seek #1, RN:Get #1, , RECORD
If Mid#(RECORD,5,4)=TYPE$ Then Write #2 Mid$(RECORD,11, 59)
RN=RN+1:Goto Loop 1
End
```

Fluid Description List File Format:
"Fluid Name Description 1"
"Fluid Name Description 2"
"Fluid Name Description n"

1

Figure 2: Creation of Fluid Property List Files:

[A "Property.Dat" file is manually keyed for each category of fluid property that lists the types of Property values available for each category of properties available in the fluid properties database.]

Property List File Format:
"Fluid Property Description 1"
"Fluid Property Description 2"
"Fluid Property Description n"

2

Figure 3: Creation of Record Number Reference File:

[A RECNUM.DAT file is created using the following code on the database which is formatted so a fluid's properties are all together.]
```
Dim RECORD as String * 80:RN=1
Open "SOURCE.DAT" for Random as #1 Len=80
Open "RECNUM.DAT" for Output as #2
Loop1: Seek #1, RN:Get #1, , RECORD
DIPPRNUM=Val(Mid#(RECORD,1,4)
If DIPPRNUM<>LASTNUM Then Write #2, DIPPRNUM, RN
LASTNUM=DIPPRNUM
RN=RN+1:Goto Loop 1
End
```

Record Number File Format:
Database Number 1, Record Number 1
Database Number 2, Record Number 2
Database Number n, Record Number n

3

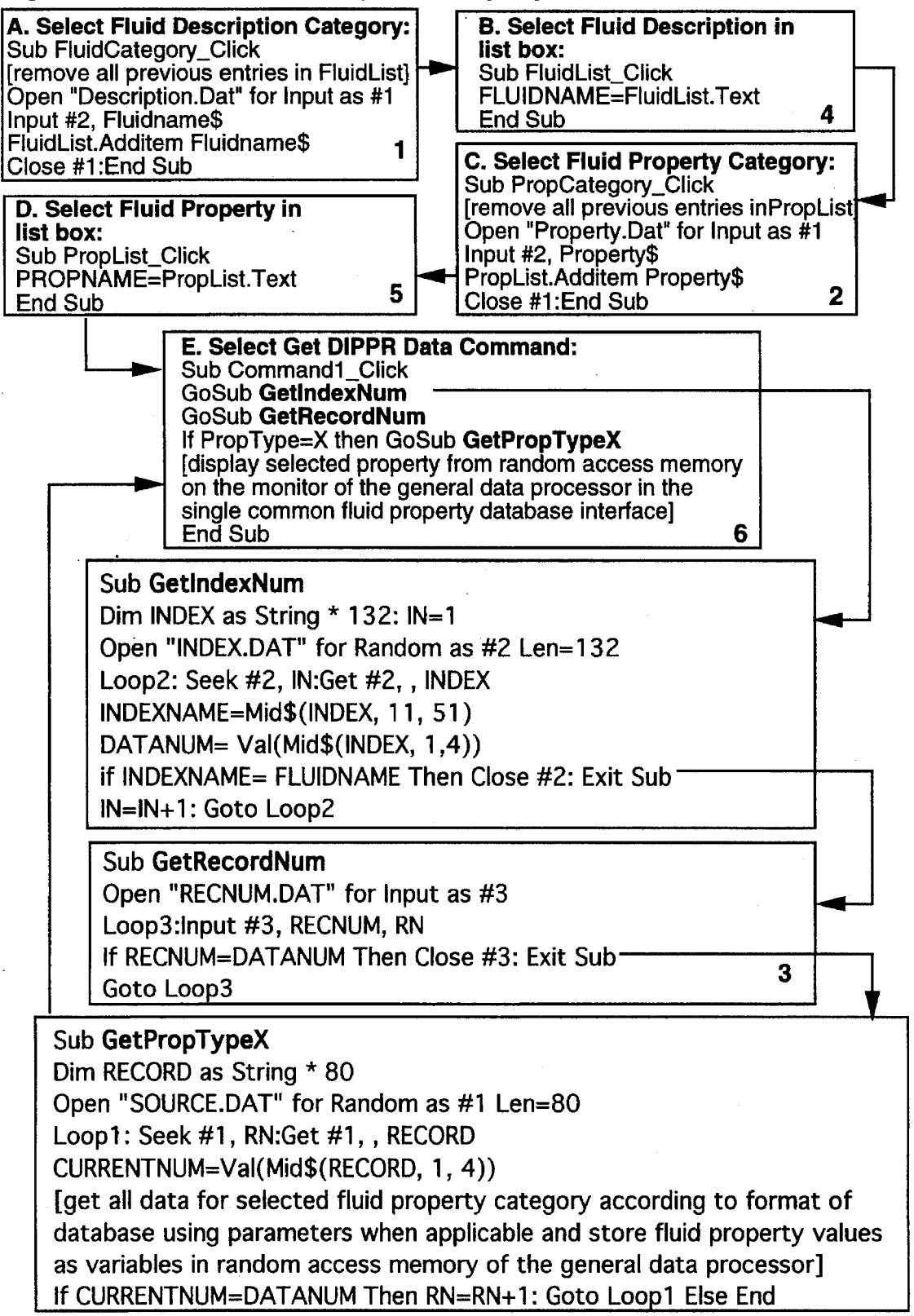

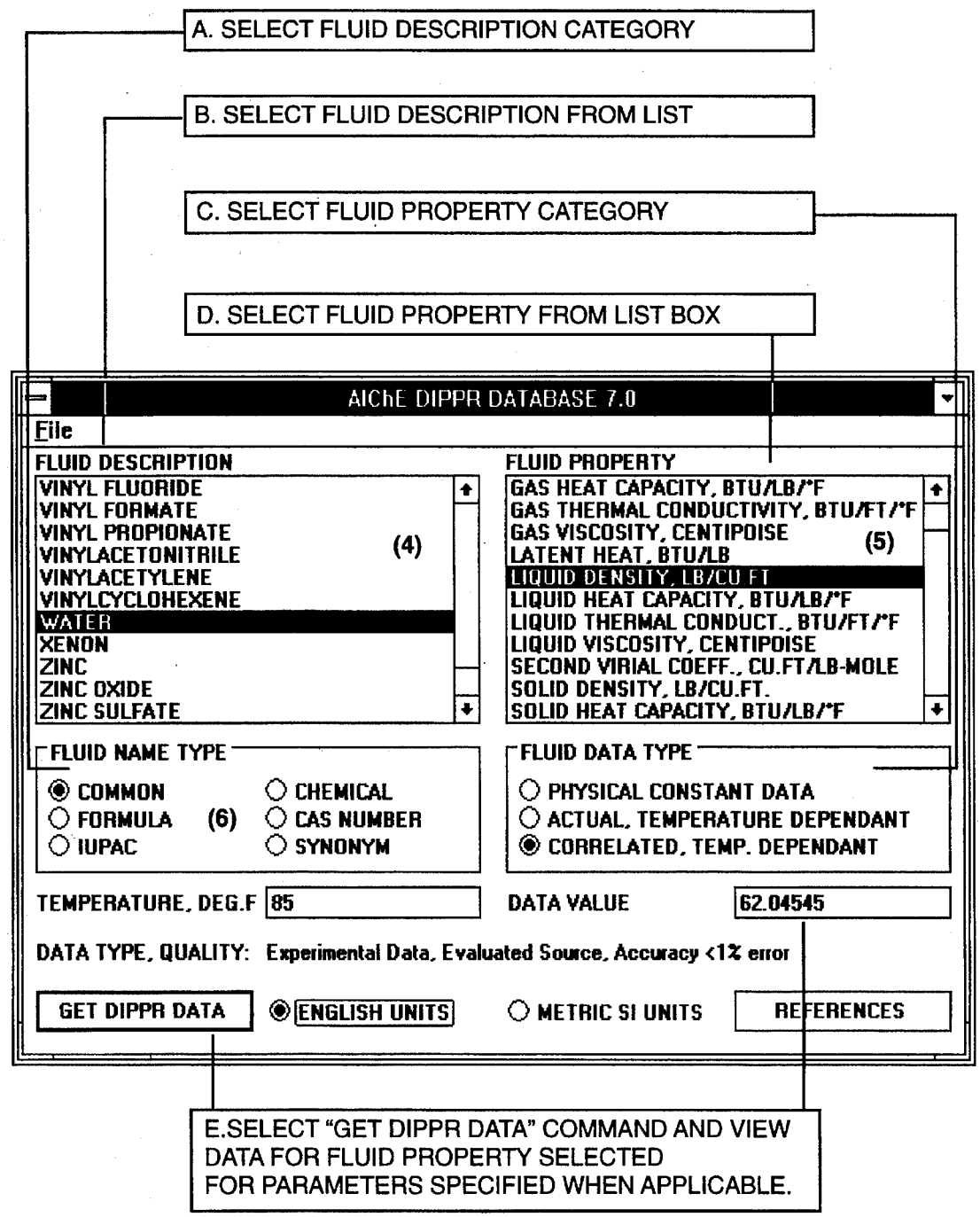
Figure 5: Single Common Fluid Property Database Interface

PHYSICAL PROPERTY DATABASE RETRIEVAL SYSTEM

BACKGROUND—FIELD OF THE INVENTION

The present invention relates to database retrieval applications and more specifically to engineering fluid property database retrieval from a developed fluid property database.

BACKGROUND OF THE INVENTION—PRIOR ART

The AIChE DIPPR database contains 39 constant and temperature dependent properties for 1284 fluids with thermodynamic, physical, and transport property data given for pure chemicals of high industrial priority. The database was prepared by the Pennsylvania State University for the Design Institute for Physical Property Data (DIPPR) which is a cooperative project sponsored by 25 major chemical manufacturers and related companies under the auspices of the American Institute of Chemical Engineers (AIChE) and copyrighted by the AIChE for distribution through authorized distributors. The Fortran data retrieval system for the DIPPR database supplied by DIPPR was originally developed for use with punch cards on a mainframe computer of the early 1980's. Distributors of the DIPPR database have traditionally relied heavily on this outdated interface for retrieval of the DIPPR data. Retrieving DIPPR fluid properties data through this computer access program requires keyboard input of the desired selection from a list of choices at least seven different times to retrieve just a single data value. To retrieve the molecular weight of a fluid from DIPPR using the Fortran supplied retrieval system, the output file name is specified, the option mode to select the fluid is selected, the type of fluid description name is entered, the fluid name is entered, the mode is switched to quit fluid description entry, the mode is switched to retrieve fluid properties, the fluid property type needs to be entered, and then the data result is displayed. For temperature dependent fluid property data, additional steps are also involved. If the fluid type is changed, the process has to be repeated from the beginning. Even if the same fluid is being used, several steps must be repeated to retrieve another data value, and the database needs to be read for each new data value requested. These types of interfaces for the DIPPR database have prevented the widespread use of this widely renowned fluid property database due to the relative difficultly associated with retrieving any fluid property data using outdated interface designs. The lack of an efficient data retrieval system to retrieve the fluid property data has also required more of the general data processor being used for data retrieval than is necessary, as well.

SUMMARY OF THE INVENTION—OBJECTS AND ADVANTAGES

The Invention consists of a single common fluid property database interface along with unique reference files to allow for the retrieval of all data for a particular fluid property category with only one reading of the DIPPR database or any other fluid property database of similar format residing on the hard disk storage area of a generic data processor. The general data processor is a personal computer system designed to operate under the MSDOS®, Windows®, or Macintosh® operating systems and would consist of a display monitor, keyboard, mouse pointing device, printer, and central processing unit with random access memory, floppy disk drive, and hard disk drive. The single common fluid property database interface consists of a list box for selecting the fluid description and a list box for selecting the fluid property. The selections in each list box change according to the category that is selected for each list through option buttons or menus. Once the desired fluid description and fluid property have been selected, a single command will retrieve the fluid property data in one reading of the fluid property database using a unique record number reference file and the results displayed on the single common fluid property database interface for each fluid property as it is selected from the list box without again reading the fluid property database until either the fluid description or fluid property category is changed. The example given earlier to retrieve the molecular weight of a fluid would only require three selections using this fluid property database retrieval system utilizing the default settings versus seven steps for the DIPPR supplied Fortran retrieval system. The use of a modern computer interface design including list boxes, option buttons, pull-down menus, and command buttons in the single common fluid property database retrieval interface allows the user to become quickly efficient in using this system since these designs are found in many other commercial software packages that are commonly used on current graphical-based operating systems such as Microsoft Windows®. These interface designs have proven to provide increased use and proficiency over single step keyboard entry systems as is used in MSDOS® and the DIPPR supplied Fortran retrieval system. Additionally, the use of a record number reference file to require only one reading of the fluid property database for a particular fluid description and fluid property category reduces the requirements of the general data processor to efficiently retrieve fluid property data from the DIPPR fluid property database.

BRIEF DESCRIPTION OF THE DRAWINGS

Other advantages of the invention become apparent upon reading the following detailed description and upon referral to the drawings of which:

FIG. 1 describes the method to create a text file for each category of fluid descriptions to provide the selections available in the fluid description list box.

FIG. 2 describes the method to create a text file for each category of fluid properties to provide the selections available in the fluid property list box.

FIG. 3 describes the method to create a record number reference file that is used to open the fluid property database at the point where the selected fluid's property data begins.

FIG. 4 is a block diagram describing the method of retrieving all fluid property data for a particular fluid and fluid property category in one reading of the database using the files created in FIG. 1–3.

FIG. 5 is a diagram which describes the single common fluid property database interface to retrieve and display fluid properties.

REFERENCE NUMERALS IN DRAWINGS

1. Fluid Description List Files
2. Fluid Property List Files
3. Record Number Reference File
4. Fluid Description List Box
5. Fluid Property List Box
6. Get DIPPR Data Command Button While the invention is susceptible to various modifications and alternative forms, a specific embodiment of the invention is described in detail below. This description is not intended to limit the invention to the particular form disclosed, but the invention is to cover all modifications and alternatives falling within the scope of the invention as defined by the claims below. Such modifications could include the use of menus to select the description and property categories instead of option buttons, the use of keyboard commands instead of selecting a command button to search the fluid property database, etc.

DESCRIPTION OF PREFERRED EMBODIMENT

Three custom files are required for the use of the process described below. To assign names to the fluid description list box 4, the creation of a text file 1 for each category of fluid descriptions that are available in DIPPR or any other fluid property database being used is required as shown in FIG. 1. These files 1 are created using a temporary utility program which searches the DIPPR SOURCE.DAT file or main fluid property database file for a particular fluid description category and then writes all occurrences for each format TYPE$ to a text file 1 for each category with one line in the text file 1 representing each fluid description in string format. Next, the creation of a text file 2 for each category of fluid properties available in the fluid properties database is required to assign names to the fluid properties list box 5 as detailed in FIG. 2. This is manually keyed for each fluid property category type to provide one line in the text file 2 for each fluid property that is available in string format. When a fluid description or fluid property category item is selected by either option buttons or menu choices, the appropriate text file corresponding to the selected category is read from the hard disk storage area of the general purpose data processor and these string values are assigned as the new selections in the appropriate list box as shown in FIG. 4 steps A & C.

To limit the reading of the DIPPR database or any other fluid property database to only the selected fluid's data, the creation of a record number reference file 3 which lists each fluid DIPPR reference or database reference number next to the first record number where that fluid's property data appears in the database is required as shown in FIG. 3. This is done using a temporary utility program which is designed to read the entire DIPPR SOURCE.DAT file or main fluid property database file and to write the first occurrence of each DIPPR database reference number or other fluid property database reference number and its current record number to the RECNUM.DAT text file 3. Since the DIPPR database is formatted so that all data for a particular fluid are grouped together, the utility program skips each data line following the first occurrence of the DIPPR reference number until another DIPPR reference number is encountered. The assignment of LASTNUM=DIPPRNUM in FIG. 3 allows for the capture of the reference number of the last record in the database so that it can be compared to the newly assigned DIPPRNUM in the next record number of RN=RN+1. If these values are not equal, then a new reference number has been found which marks the beginning of another fluid's properties and this reference number and its record number is written to the RECNUM.DAT file 3. This process is repeated until the entire database has been scanned and the record number reference file 3 is completed. For fluid property databases which do not group each fluid's properties all together, the database records would need to be reorganized accordingly before creation of the record number reference file 3 as detailed above.

The process of retrieving fluid property data can now begin as is detailed in FIG. 4. When the fluid description category is changed, the current selections in the fluid description list box 4 "FluidList" are removed and the Description.Dat file 1 which corresponds to the selected category that was created earlier in FIG. 1 is opened and its string values assigned as the new selections available in the fluid description list box 4 "FluidList". Then when the "FluidList" fluid description list box 4 is clicked on or selected the subroutine FluidList_Click is invoked which assigns the selected item in the list "FluidList.Text" to the string variable FLUIDNAME in the random access memory of the general data processor as detailed in FIG. 4 steps A and B.

When the fluid property category is changed, the current selections in the fluid property list box 5 "PropList" are removed and the Property.Dat file 2 which corresponds to the selected category which was created earlier in FIG. 2 is opened and its string values assigned as the new selections available in the fluid property list box 5 "PropList". Then when the "PropList" fluid property list box 5 is clicked on or selected the subroutine PropList_Click is invoked which assigns the selected item in the list "PropList.Text" to the string variable PROPNAME in the random access memory of the general data processor as detailed in FIG. 4 steps C and D.

When selections have been made in the fluid description list box 4 and the fluid property list box 5, the Get DIPPR Data command 6 or equivalent command can then be selected as detailed in FIG. 4 step E. The GetIndexNum subroutine is invoked first which opens the DIPPR INDEX.DAT file on the hard disk storage area of the general data processor as a random file of length=132 and then scans this file until the area assigned for fluid descriptions (location 11 thru 51) matches the FLUIDNAME string variable assigned by the fluid description list box 4 in the FluidList_Click subroutine. When a match is found, the DIPPR reference number is retrieved (location 1 thru 4) and assigned to the variable DATANUM. Then the GetRecordNum subroutine is invoked which opens the RECNUM.DAT record number reference file 3 created in FIG. 3. This file is scanned until the RECNUM record number in the RECNUM.DAT file matches the DATANUM which corresponds to the fluid description selected in the fluid description list box 4. When a match is found, the record number RN next to the RECNUM reference number can then be used to open the SOURCE.DAT file or main fluid property database file at the precise record number where the selected fluid's property data begins.

Then, the GetPropTypen subroutine is invoked which opens the SOURCE.DAT or main fluid property database file at the record number RN assigned by the GetRecordNum subroutine. All the data for the selected fluid property category is then retrieved according to the format of the database being used. Parameters are used when applicable and the retrieved values of the fluid property data are stored as variables in the random access memory of the general data processor. The database is read as long as the CURRENTNUM representing the current database reference number equals the DATANUM representing the reference number of the fluid selected in the fluid description list box 4. When CURRENTNUM does not equal the DATANUM, then all data on the selected fluid has been exhausted and the database is closed. The fluid properties are then displayed on a single common fluid property database interface shown in FIG. 5 from the random access memory of the general data processor as a fluid property is selected from the fluid property list box 5 without again reading the fluid properties database unless the fluid description or fluid property category is changed. This method provides direct access of all fluid property data while requiring the minimum amount of time required by the general data processor to read the DIPPR SOURCE.DAT file.

The steps in the single common fluid property database interface to retrieve fluid property data from the hard disk storage area of a general data processor shown in FIG. 5 relate to the steps shown in FIG. 4. First the fluid description category is selected and the fluid description selected from the fluid description list box 4 which corresponds to steps A and B in FIGS. 4 and 5. Then the Fluid category is selected and the fluid property selected from the fluid property list box 5 which corresponds to steps C and D in FIGS. 4 and 5. When the Get DIPPR Data command 6 is selected, step E in FIG. 4 and FIG. 5 is invoked to retrieve the fluid property data and display the results on the single common fluid property database interface. Then any fluid property in the current fluid property list can be immediately displayed from the random access memory of the general data processor by selecting an item from the fluid property list box 5.

In summary, this process of retrieving fluid property data in one reading of the database with the single common fluid property database interface utilizing a unique record number reference file 3 provides quicker and easier access to the fluid property data in the DIPPR database whose data is vital in the design and optimization of process systems in the process industries. This process could also be useful for other types of databases which can be formatted to the format used by the DIPPR database.

What is claimed is:

1. A process of data retrieval of physical properties of an element from an existing physical property database residing on a hard disk storage area of a general data processor with random access memory to enable said general data processor to retrieve all said physical properties of a physical property description category in one reading of said existing physical property database and to display said physical properties using a single common physical property database interface displayed on a display monitor of said general data processor without making any format structure modifications to said existing physical property database, said process comprising the steps of:

a. creating and storing in said hard disk storage area an element description list file for each element description category available in said existing physical property database;

b. displaying on said display monitor the description of each said element of a selected said element description list file in an element description list box within said single common physical property database interface;

c. selecting an element from said element description list box displayed on said display monitor wherein element descriptions listed in said element description list box change when a said element description category is changed;

d. creating and storing in said hard disk storage area a physical property list file for each said physical property description category available in said existing physical property database;

e. displaying on said display monitor the description of each said physical property of a selected said physical property list file in a physical property list box within said single common physical property database interface;

f. selecting said physical properties of said selected element from said physical property list box displayed on said display monitor wherein said physical property list box changes when said physical property description category is changed;

g. generating and storing on said hard disk storage area a unique record number reference file for said existing physical property database;

h. identifying a record number to begin searching for said physical properties within said existing physical property database residing on said hard disk storage area of said general data processor for said selected element utilizing said unique record number reference file;

i. retrieving all of said physical properties in said existing physical property database for said selected element with a single read of said existing physical property data base and storing said physical properties in said random access memory using a single command on said single common physical database interface; and j. displaying on said display monitor said stored physical properties as said physical properties are selected within said physical property list box without again having to read said existing physical property database.

* * * * *